US00PP19712P2

(12) United States Plant Patent
Henny et al.

(10) Patent No.: US PP19,712 P2
(45) Date of Patent: Feb. 10, 2009

(54) ***AGLAONEMA* PLANT NAMED 'UF25712KL'**

(50) Latin Name: *Aglaonema commutatum*
Varietal Denomination: UF25712KL

(75) Inventors: Richard J. Henny, Tavares, FL (US); Jianjun J. Chen, Apopka, FL (US)

(73) Assignee: Florida Foundation Seed Producers Inc., Greenwood, FL (US)

( * ) Notice: Subject to any disclaimer, the term of this patent is extended or adjusted under 35 U.S.C. 154(b) by 0 days.

(21) Appl. No.: 12/074,406

(22) Filed: Mar. 3, 2008

(51) Int. Cl.
*A01H 5/00* (2006.01)

(52) U.S. Cl. ..... Plt./376
(58) Field of Classification Search ..... Plt./376
See application file for complete search history.

*Primary Examiner*—Kent L Bell
(74) *Attorney, Agent, or Firm*—C. A. Whealy

(57) ABSTRACT

A new and distinct cultivar of *Aglaonema* plant named 'UF25712KL', characterized by its large and upright plant habit; vigorous and dense growth habit; dark green-colored leaves with grey green-colored venal areas with the center of the leaf suffused with yellow green-colored spots; and white-colored petioles.

2 Drawing Sheets

Botanical designation: *Aglaonema commutation.*
Cultivar denomination: 'UF25712KL'.

BACKGROUND OF THE INVENTION

The present invention relates to a new and distinct cultivar of *Aglaonema* plant, botanically known as *Aglaonema commutatum,* and hereinafter referred to by the name 'UF25712KL'.

The objective of the Inventors' breeding program is to create new *Aglaonema* cultivars that have uniform plant habit, exceptional performance and unique and attractive foliage coloration.

The new *Aglaonema* originated from a cross-pollination made by the Inventors in Apopka, Fla. of an unnamed proprietary selection of *Aglaonema commutatum,* not patented, as the female, or seed, parent with the *Aglaonema commutatum* cultivar Curtissi, not patented, as the male, or pollen, parent. The new *Aglaonema* was discovered and selected by the Inventors as a single plant within the progeny of the stated cross-pollination in a controlled environment in Apopka, Fla.

Asexual reproduction of the new cultivar by tip cuttings in a controlled environment in Apopka, Fla. has shown that the unique features of this new *Aglaonema* are stable and reproduced true to type in successive generations of asexual reproduction.

SUMMARY OF THE INVENTION

The cultivar UF25712KL has not been observed under all possible environmental conditions. The phenotype may vary somewhat with variations in environment such as temperature and light intensity, without, however, any variance in genotype.

The following traits have been repeatedly observed and are determined to be the unique characteristics of 'UF25712KL'. These characteristics in combination distinguish 'UF25712KL' as a new and distinct cultivar of *Aglaonema:*

1. Large and upright plant habit.
2. Vigorous and dense growth habit.

3. Dark green-colored leaves with grey green-colored venal areas with the center of the leaf suffused with yellow green-colored spots.
4. White-colored petioles.

Plants of the new *Aglaonema* differ from plants of the female parent selection in the following characteristics:

1. Plants of the new *Aglaonema* are larger and more upright than plants of the female parent selection.
2. Plants of the new *Aglaonema* and the female parent selection differ in leaf color as plants of the female parent selection have green-colored leaves.
3. Plants of the new *Aglaonema* and the female parent selection differ in petiole color as plants of the female parent selection have pink-colored petioles.

Plants of the new *Aglaonema* differ from plants of the male parent, the cultivar Curtissi, in the following characteristics:

1. Plants of the new *Aglaonema* and the cultivar Curtissi differ in leaf color as plants of the cultivar Curtissi have green-colored leaves.
2. Plants of the new *Aglaonema* and the cultivar Curtissi differ in petiole color as plants of the cultivar Curtissi have green-colored petioles.

Plants of the new *Aglaonema* can also be compared to plants of the cultivar Superba, disclosed in U.S. Plant Pat. No. 7,501. In side-by-side comparisons conducted in Apopka, Fla. plants of the new *Aglaonema* differed from plants of the cultivar Superba in the following characteristics:

1. Plants of the new *Aglaonema* were more compact than plants of the cultivar Superba.
2. Plants of the new *Aglaonema* had smaller leaves than plants of the cultivar Superba.
3. Leaves of plants of the new *Aglaonema* were more upright than leaves of plants of the cultivar Superba.

BRIEF DESCRIPTION OF THE PHOTOGRAPHS

The accompanying photographs illustrate the overall appearance of the new *Aglaonema.* These photographs show the colors as true as it is reasonably possible to obtain in colored reproductions of this type. Colors in the photographs may differ slightly from the color values cited in the detailed botanical description which accurately describe the colors of the new *Aglaonema.*

The photograph on the first sheet is a side perspective view of a typical plant of 'UF25712KL' grown in a container.

The photograph on the second sheet is a close-up view of the upper (left) and lower (right) surfaces of a typical leaf of 'UF25712KL'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in containers in Apopka, Fla. during the summer and early autumn in a polyethylene-covered greenhouse. Plants were grown under conditions and practices which approximate those generally used in commercial *Aglaonema* production. During the production of the plants, day temperatures ranged from about 29° C. to 35° C., night temperatures ranged from about 18° C. to 26° C. and light levels were about 3,000 foot-candles. Plants were about 18 months old when the photographs and the detailed description were taken.

Botanical classification: *Aglaonema commutatum* cultivar UF25712KL.

Parentage:

*Female, or seed, parent.*—Unnamed proprietary selection of *Aglaonema commutatum,* not patented.

*Male, or pollen, parent.*—*Aglaonema commutatum* cultivar Curtissi, not patented.

Propagation:

*Type.*—By tip cuttings.

*Time to initiate roots, summer.*—About 21 to 24 days at 25° C. to 35° C.

*Time to initiate roots, winter.*—About 35 to 40 days at 15° C. to 28° C.

*Time to produce a rooted young plant, summer.*—About 35 to 40 days at 25° C. to 35° C.

*Time to produce a rooted young plant roots, winter.*—About 45 to 50 days at 15° C. to 28° C.

*Root description.*—Abundant fleshy whitish-colored roots with finer lateral roots.

Plant description:

*Plant/growth habit.*—Tall and upright plant habit; inverted triangle. Vigorous, dense growth habit; suitable for 20-cm to 25-cm containers. New leaves initially upright, then arching outwardly with development.

*Plant height, from soil level to top of leaf plane.*—About 68 cm to 76 cm.

*Plant diameter or spread.*—About 59 cm to 66 cm.

*Stem description.*—Branching habit: Plants of the new *Aglaonema* are freely basal branching with about eight basal branches developing per plant. Aspect: Mostly upright. Strength: Strong. Length, soil level to junction to two youngest leaves: About 31 cm to 43 cm. Diameter: About 2.4 cm. Internode length: About 7 mm to 10 mm. Color, immature: Between 145D and 155C; faintly mottled with 144C to 144D. Color, mature: 145C mottled with 144B; with further development, 165C to 165D mottled with 144B.

*Cataphylls.*—Length: About 9 cm to 11 cm. Width: About 2.4 cm. Shape: Lanceolate, keeled. Apex: Cuspidate to mucronate. Base: Clasping the stem. Color, inner and outer surfaces: Between 155A and 158C to 158D; towards the apex, variably spotted with 146B.

Foliage description:

*Arrangement.*—Alternate/whorled; simple.

*Length.*—About 27.2 cm to 34.5 cm.

*Width (flattened).*—About 9 cm to 12.2 cm.

*Shape.*—Elliptic.

*Apex.*—Acuminate.

*Base.*—Acute.

*Margin.*—Entire; mostly flat with some broad undulations.

*Texture, upper and lower surfaces.*—Smooth, glabrous.

*Venation pattern.*—Pinnate.

*Color.*—Developing leaves, upper surface: Ground color, between 147A to 137B; venal areas, 191B to 191C; center of leaf variably spotted with 145D, 150D and 155A. Venation: Midrib, 145C to 145D mottled with 144A to 144B; primary veins, 154C to 154D or 191B to 191C. Developing leaves, lower surface: Ground color, between 147B to 146C; random speckles or mottling, 145B to 145C, 155A or 157C; venal areas, mottled with 157C or 145C to 145D. Venation: Midrib, 150D; primary veins, 145C to 145D. Fully expanded leaves, upper surface: Ground color, between 147A to N189A; venal areas, 191C; center of leaf variably spotted with 154D, 144A and 144B. Venation: Midrib, 154C to 154D streaked or mottled with 144A to 144B; primary veins, 154C to 154D or 191C. Fully expanded leaves, lower surface: Ground color, between 147B to 147C and 146B; random speckles or mottling, 155A, 157B to 157C or 145C to 145D; venal areas, mottled with 157B to 157C or 145C to 145D. Venation: Midrib, 155B; primary veins, 145C to 145D.

*Petiole.*—Aspect: Mostly erect, outwardly arching to about 30° from vertical with development. Length: About 20 cm. Diameter, distal: About 6.5 mm. Diameter, proximal, flattened: About 4.8 cm. Strength: Strong; flexible. Color, distal: 155A to 155C. Color, proximal: 155A; area adjacent to stem, 155D often faintly tinged with 164D. Wing length: About 18 cm. Wing diameter, base: About 2.4 cm. Wing color, inner surface: 155C. Wing color, outer surface: 155A; area adjacent to stem, 155D often faintly tinged with 164D.

Inflorescence description: Inflorescences are not often observed on plants of the new *Aglaonema.*

Disease/pest resistance: Plants of the new *Aglaonema* have not been observed to be resistant to pathogens or pests common to *Aglaonema.*

Temperature tolerance: Plants of the new *Aglaonema* have been observed to be tolerant to temperatures ranging from about 13° C. to about 40° C. for several hours.

It is claimed:

1. A new and distinct *Aglaonema* plant named 'UF25712KL' as illustrated and described.

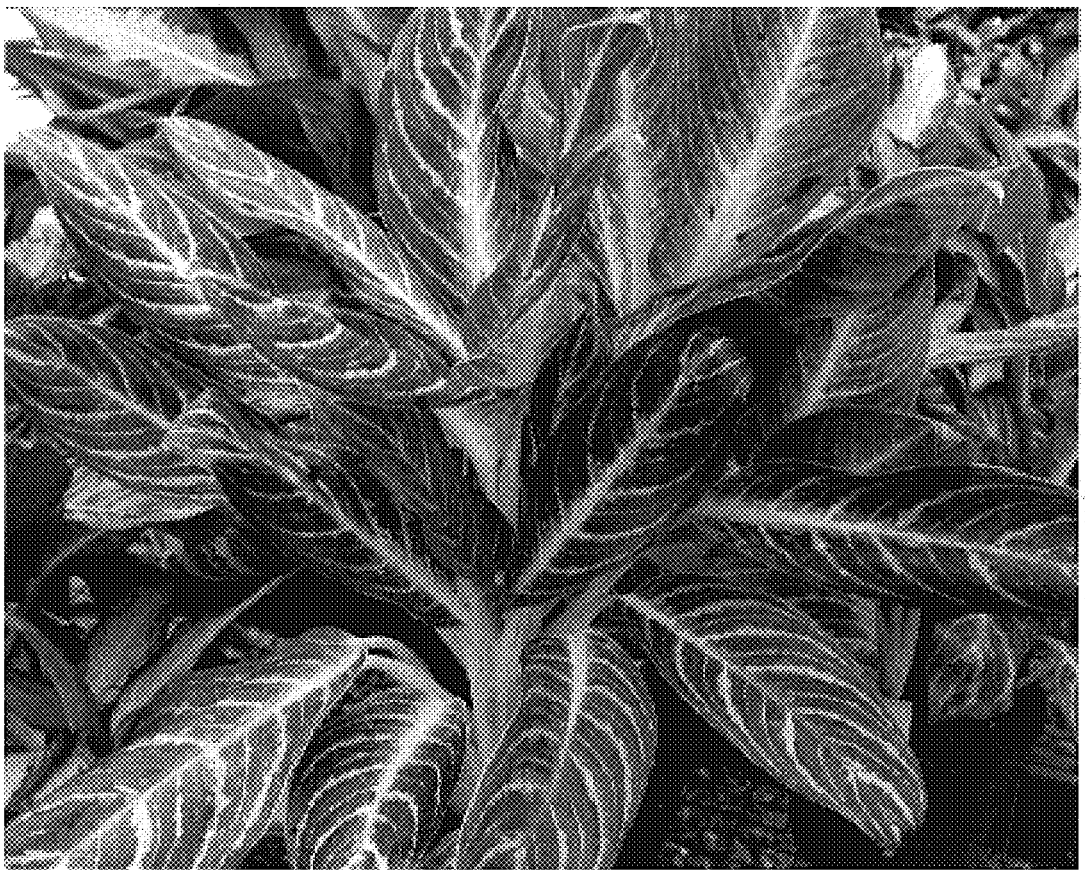

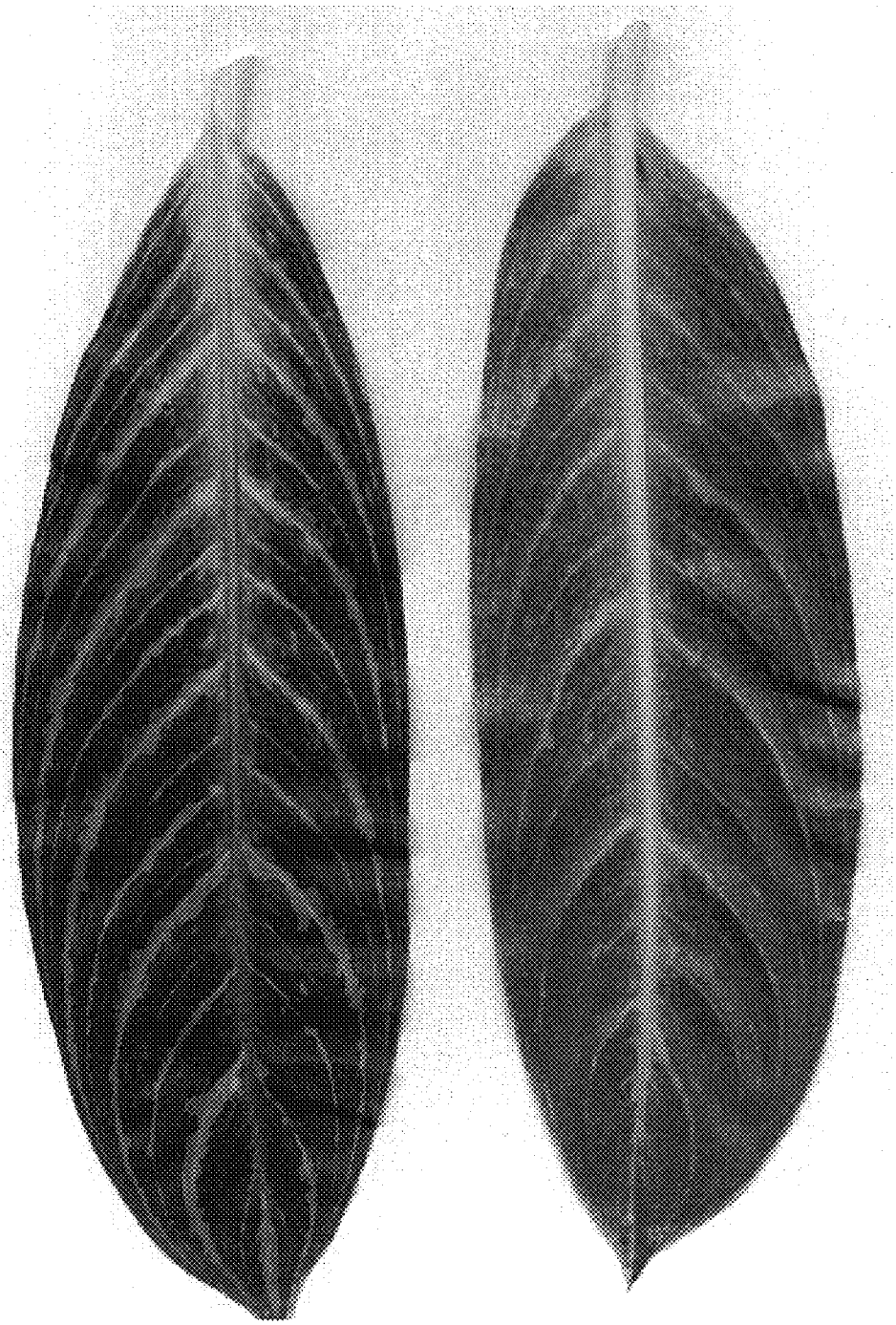

* * * * *